United States Patent
Haines et al.

(10) Patent No.: US 9,702,772 B2
(45) Date of Patent: Jul. 11, 2017

(54) SURFACE ACOUSTIC WAVE (SAW) BASED STRAIN SENSOR

(71) Applicant: Mnemonics, Inc., Melbourne, FL (US)

(72) Inventors: D Mark Haines, Melbourne, FL (US); Robert J. Peterman, Manhattan, KS (US); Nicholas Kozlovski, Orlando, FL (US)

(73) Assignee: Mnemonics, Inc., Melbourne, FL (US)

(*) Notice: Subject to any disclaimer, the term of this patent is extended or adjusted under 35 U.S.C. 154(b) by 74 days.

(21) Appl. No.: 14/669,579

(22) Filed: Mar. 26, 2015

(65) Prior Publication Data

US 2016/0282204 A1   Sep. 29, 2016

Related U.S. Application Data

(60) Provisional application No. 61/970,759, filed on Mar. 26, 2014.

(51) Int. Cl.
 *G01N 29/04* (2006.01)
 *G01L 1/16* (2006.01)
 (Continued)

(52) U.S. Cl.
 CPC ............ *G01L 1/165* (2013.01); *G01K 11/265* (2013.01); *G01L 9/008* (2013.01); *G01L 9/0025* (2013.01);
 (Continued)

(58) Field of Classification Search
 CPC ....... G01L 1/165; G01L 9/0025; G01L 9/008; G01L 19/0092; G01N 2291/0423;
 (Continued)

(56) References Cited

U.S. PATENT DOCUMENTS

| 3,978,731 A | 9/1976 | Reeder |
| 4,096,740 A | 6/1978 | Sallee |

(Continued)

FOREIGN PATENT DOCUMENTS

| JP | 03250810 A | * | 11/1991 |
| KR | 20020072056 A | * | 9/2002 |

OTHER PUBLICATIONS

Scholl, et al. "Wireess Passive Saw Sensor Systems for Industrial and Domestic Applications", IEEE, International Frequency and Control Symposium, 1998, p. 595-601.

(Continued)

*Primary Examiner* — Jonathan Dunlap
(74) *Attorney, Agent, or Firm* — Beusse, Wolter, Sanks, & Maire, PLLC; John L. DeAngelis

(57) ABSTRACT

A sensor system for determining deformation of an object subject to forces. The sensor system comprises an object upon which forces are exerted and a cavity within the object, a first substrate for supporting surface acoustic waves in an upper surface of the first substrate, the first substrate disposed in the cavity, a first surface acoustic wave transducer disposed on the upper surface and responsive to an interrogation signal for generating an incident surface acoustic wave in the upper surface, a first reflector array responsive to the incident surface acoustic wave for creating reflected surface acoustic waves on the upper surface, the reflected surface acoustic waves received by the transducer and having characteristics indicative of strain deformation of the object due to a force exerted on the object.

16 Claims, 4 Drawing Sheets

(51) Int. Cl.
*G01L 9/00* (2006.01)
*G01K 11/26* (2006.01)
*G01L 19/00* (2006.01)

(52) U.S. Cl.
CPC ........ *G01L 19/0092* (2013.01); *G01N 29/041* (2013.01); *G01N 2291/011* (2013.01); *G01N 2291/0422* (2013.01); *G01N 2291/0423* (2013.01); *G01N 2291/106* (2013.01)

(58) Field of Classification Search
CPC ..... G01N 2291/011; G01N 2291/0422; G01N 2291/106; G01N 29/041; G01K 11/265
USPC ............ 73/579, 597, 801, 514.28, 587, 627; 374/117, 119; 310/313 B, 313 R, 313 D
See application file for complete search history.

(56) References Cited

U.S. PATENT DOCUMENTS

| | | | |
|---|---|---|---|
| 4,100,811 A | 7/1978 | Cullen | |
| 4,467,235 A * | 8/1984 | De Wames | G01H 13/00 310/313 B |
| 4,623,813 A | 11/1986 | Naito | |
| 5,821,425 A | 10/1998 | Mariani | |
| 6,186,005 B1 * | 2/2001 | Leidl | G01N 29/022 310/313 A |
| 6,484,582 B2 * | 11/2002 | Ehrfeld | F16C 19/522 384/448 |
| 6,810,750 B1 | 11/2004 | Kiefer | |
| 7,109,632 B2 | 9/2006 | van Knokke | |
| 7,165,455 B2 | 1/2007 | Magee | |
| 7,243,547 B2 * | 7/2007 | Cobianu | G01L 9/0025 310/313 B |
| 7,915,785 B2 * | 3/2011 | Andle | G01D 5/48 310/313 D |
| 2002/0062694 A1 * | 5/2002 | Ehrfeld | F16C 19/522 73/593 |
| 2006/0075820 A1 * | 4/2006 | Cobianu | G01L 9/0025 73/703 |
| 2006/0123913 A1 | 6/2006 | Marsh | |
| 2006/0130585 A1 | 6/2006 | Magee | |
| 2007/0120623 A1 * | 5/2007 | Sakiyama | H03H 9/02834 333/133 |
| 2008/0190169 A1 * | 8/2008 | Naum | G01N 29/30 73/1.82 |
| 2008/0265711 A1 * | 10/2008 | Kumar | G01L 9/0025 310/313 B |
| 2010/0043560 A1 * | 2/2010 | Andle | G01D 5/48 73/654 |
| 2012/0036917 A1 * | 2/2012 | Avramescu | G01N 29/022 73/24.04 |
| 2012/0125118 A1 | 5/2012 | Cobianu | |
| 2013/0026882 A1 | 1/2013 | Yamada | |
| 2013/0036821 A1 * | 2/2013 | Belkerdid | G01N 29/041 73/627 |
| 2013/0205906 A1 * | 8/2013 | Chommeloux | G01L 9/0025 73/702 |
| 2015/0013461 A1 | 1/2015 | Pollard | |
| 2015/0013468 A1 * | 1/2015 | Johnson | G01N 3/08 73/778 |

OTHER PUBLICATIONS

Aubert, et al., "Wireless and Batteryless Surface Acoustic Wave Sensors for High Temperature Environments", The Ninth International Conference on Electronic Measurement & Instruments, ICEMI, 2009, p. 890-898.

Kalinin, Passive Wireless Strain and Temperature Sensors Based on SAW Devices, Radio and Wireless Conference, IEEE, 2004, p. 187-190.

McCormack, Modeling of Surface Acoustic Wave Strain Sensors Using Coupling-of-Modes Analysis, IEEE, vol. 58 No. 11, 2011, Pg.

* cited by examiner

SURFACE ACOUSTIC WAVE (SAW) BASED STRAIN SENSOR

CROSS REFERENCE TO RELATED APPLICATION

This patent application claims benefit of the Mar. 26, 2014 filing date of provisional patent application No. 61/970,759, which is incorporated by reference herein.

FIELD OF THE INVENTION

The present invention relates to surface acoustic wave devices (SAW devices) and specifically to SAW devices for use in measuring material strain deformation due to stress forces imposed on a body or a material.

BACKGROUND OF THE INVENTION

Stress is related to a force imposed on a material or body and strain is the deformation of the material or body responsive to that stress force. The force that produces the stress can be a compression force or a tension force. Stress is defined as $$\sigma = F/A$$

where σ is the stress, F is the force imposed on the material or body and A is the area over which that force is exerted.

The relationship between the stress and the resulting strain as manifested by a specific material is referred to as the stress-strain curve for that material. The curve is unique for each material and relates the amount of deformation (strain) at various values of tensile or compressive loading (stress). These curves reveal many of the properties of a material, including data to establish the materials modulus of elasticity (Young's modulus).

Strain is a dimensionless quantity that is a measure of body deformation representing the displacement of particles in the body relative to a reference length or another reference dimension. Strain measures are usually expressed as a percent or a decimal fraction of the reference dimension when no stress forces are present. For example, ΔL/L is a ratio indicating strain, where ΔL is a measure of a change in a body dimension (deformations due to a compression force, for example) and L is a measure of the body dimension when no stress forces are present.

A passive SAW (surface acoustic wave) device comprises a transducer that generates an acoustic wave in response to an input signal, usually referred to as an interrogation signal. The waves propagate on the surface of a material (referred to as a substrate and which may comprise lithium niobate, for example) to a reflector array. The acoustic waves reflect from the reflector array back to the transducer where they are received and processed. The characteristics of the reflected wave are representative of physical parameters of the reflector array. For example, spacing of the reflectors of the reflector array, which affect the frequency and/or phase of the reflected signal, are affected by a temperature of the material, which may in turn be affected by an ambient temperature of the region surrounding the SAW device. The spacing of the reflectors in the reflector array are also influenced by compression and tension forces applied to the substrate.

Characteristics of the reflected waves (e.g., time delay, propagation losses, phase delay) indicate certain characteristics of the substrate or a material to which the substrate is affixed. These characteristics may include temperature (which may cause the material to expand or contract), forces exerted, and resulting stresses. As the spacing of the reflector array elements changes the frequency of the reflected wave, either primary or secondary, may also be affected. Displacement can be measured in this way.

FIG. 1 depicts a prior art SAW device 10 (also referred to as a SAW sensor). An interrogating signal comprises a radio frequency (RF) signal pulse 12 transmitted by an RF transceiver 14. The interrogating signal is received by an antenna 18 connected to an interdigital transducer (IDT) 20 disposed on a piezoelectric substrate 24. The IDT 20 launches an incident surface acoustic wave (SAW) 28 onto the piezoelectric substrate 24 in response to the received interrogating signal. The transmitted wave travels along the surface of the piezoelectric substrate 24 as illustrated in FIG. 1.

The SAW 28 propagates along the substrate 24 and is received at a reflector array 30 also disposed on the piezoelectric substrate 24. The reflector array 30 comprises a pattern of metal electrodes (also referred to as elements or reflectors) that impart an impulse response to the incident SAW 28. The impulse response of the reflector array 30 is imparted to the incident SAW 28 as it launches a reflected SAW 34 (also referred to as an echo) back to the IDT 20.

The IDT 20 receives and converts the reflected SAW 34 to an electrical signal that is then radiated from the antenna 18 back to the RF transceiver 14 for extraction of the desired information in the reflected signal.

A SAW device can sense piezoelectric crystal strain as the strain modifies physical parameters the reflector array 30 (such as the spacing between elements of the reflector array 30) and thus the reflected signal. For example, either the frequency shift of the reflected signal or the time delay of the reflected signal can be measured as an indication of the strain.

This technique provides a wireless strain sensor that can be mounted onto translating or rotating components where wire or other physical connections are not practical.

BRIEF DESCRIPTION OF THE DRAWINGS

The invention is explained in the following description in view of the drawings.

DETAILED DESCRIPTION OF THE INVENTION

Before describing in detail the particular method and apparatus related to a SAW device for determining strain experienced by an object, it should be observed that the present invention resides primarily in a novel and non-obvious combination of elements and process steps. So as not to obscure the disclosure with details that will be readily apparent to those skilled in the art, certain conventional elements and steps have been presented with lesser detail, while the drawings and the specification describe in greater detail other elements and steps pertinent to understanding the invention.

The following embodiments are not intended to define limits of the structure or method of the invention, but only to provide exemplary constructions. The embodiments are permissive rather than mandatory and illustrative rather than exhaustive.

Figure 1:
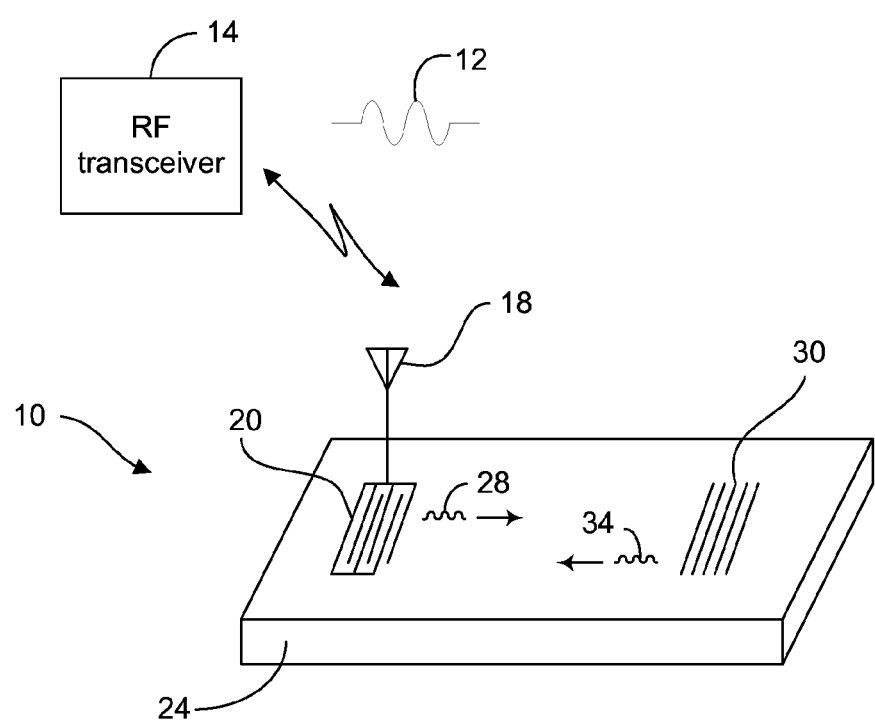
FIG. 1 illustrates a prior art surface acoustic wave device.
Figure 2:
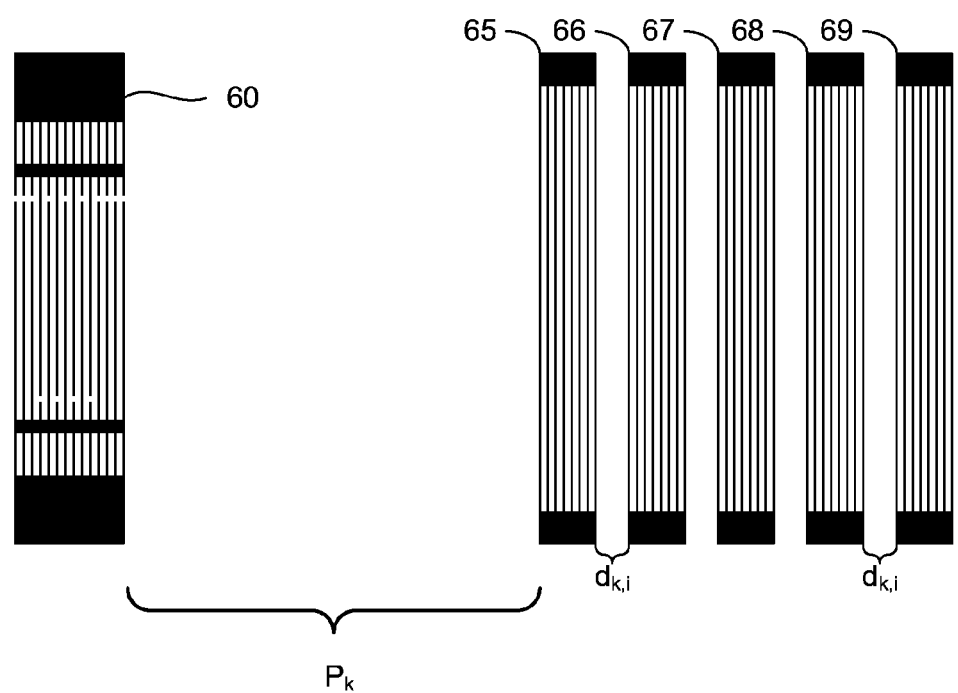
FIG. 2 illustrates a transducer (IDT) and reflector array of a SAW device.

A system of the invention comprises k SAW devices or SAW sensors with one of the k devices illustrated in FIG. 2. Each $k^{th}$ device further comprises, an IDT 60, and in one embodiment, five reflectors designated 65, 66, 67, 68 and 69. Each $i^{th}$ gap of the $k^{th}$ SAW device between two adjacent reflector electrodes is designated $d_{k,i}$. Note that there is no $d_{k,5}$ gap. Each of the k SAW sensors creates a reflected SAW or echo at the same time and collectively the k SAW sensors provide an indication of strain deformations in multiple directions. If strain deformation in only one direction is sought then a single SAW sensor to measure that strain in that direction may suffice.

Preferably the temperature of the object experiencing the strain must be determined as deformation due to an applied force and deformation due to a temperature change cannot be distinguished. A technique for resolving this issue is described below.

For each of the k devices, a first reflector 65 is located at a distance $p_k$ (also referred to as a delay line distance) from the IDT 60. Each subsequent reflector of the reflector array effectively carries a +1 or −1 code that is related to a phase shift imposed on the echo signal at each reflector that is due to changes in the spacing $d_{k,i}$ between successive reflectors. The echo from the first reflector 65 is always defined as +1 code that serves as a phase reference to allow defining the phase of the other reflector echos relative to the first reflector 65. For instance the code shown in FIG. 2 is +1, −1, −1, +1, +1 due to the gap distance $d_{k,i}$ between each reflector pair. The change in gap distances between each reflector electrode is slight and may not be easily observed in FIG. 2. But generally, beginning with the reflector electrode 65, the gap lengths are qualitatively considered as narrow, medium, wide, and medium.

Depending on the application, this approach can be referred to as code division multiple access, or CDMA, since the coding is important for correlation properties, or it can be referred to as time division multiple access, or TDMA, since the k devices occupy different time slots (i.e. $p_k$ is selected such that if all k devices were visually overlapped none of the reflectors in any of the k devices would touch).

Dimensions in such devices are typically referred to in SAW wavelengths. For example, at 915 MHz for YZ Lithium Niobate a SAW wavelength is 3.8 micrometers. Spacing between each of the reflector electrodes 65-69 varies by ±¼ wavelength to achieve the +1, −1, −1, +1, +1 code referred to above. The period of the electrode pair comprising the IDT 60 is one wavelength.

The impulse response length for each $k^{th}$ device is approximately 350 nanoseconds where the impulse length is from the leading edge of the echo from the first reflector electrode to the end of the response from the last reflector electrode. This length is the same for each $k^{th}$ sensor only the $p_k$ length changes for each $k^{th}$ sensor. To increase sensitivity to strain deformation this length can be increased by either adding additional reflectors in an array, adding additional reflector arrays or by increasing the separation between the five illustrated reflectors 65, 66, 67, 68, and 69.

Although the SAW sensor can be bonded to any surface of the object to determine strain, it has been found that to improve the predictability of the relationship between surface strain on the object and surface strain on the component-bearing side of the SAW substrate, each of the k SAW devices are disposed in a well, depression or cavity defined in a surface of the object. The SAW substrate is affixed to the surfaces of said well using a stiff adhesive or solder, i.e., a bonding material that will efficiently transfer deformations in the object to the SAW substrate. Disposing the substrate in the well allows for bonding of its bottom surface, side surfaces (e.g., the longer of the four surfaces that form the perimeter of the substrate) and end surfaces (e.g., the shorter of the four surfaces that form the perimeter of the substrate) to adjacent surfaces of the well.

By comparison, when the bottom surface of the SAW sensor is bonded to an upper surface of the object, the four sides of the substrate are not bonded or attached to anything and therefore all the strain in the object has to propagate up through the substrate to have any effect on the top surface and the propagation of the surface acoustic wave on that surface. This approach of bonding the SAW sensor in a well is considered superior to bonding only the bottom surface of the sensor to the substrate as it provides more accurate strain measurements.

Figure 3:
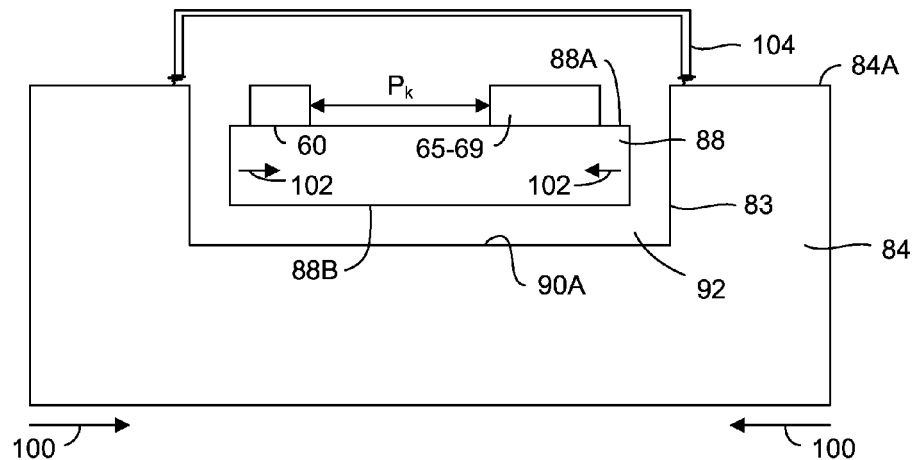
FIG. 3 illustrate a system of the present invention mounted within a well of an object that experiences strain deformation.
Figure 4:
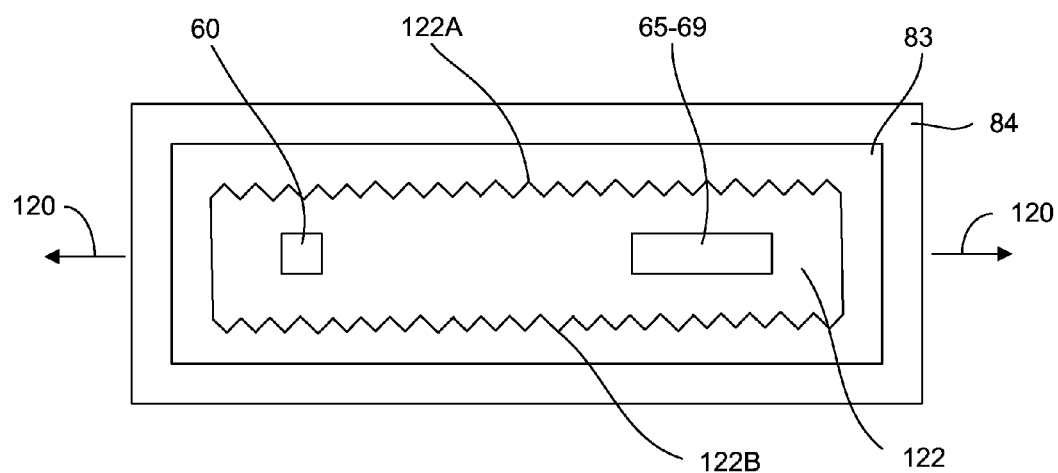
FIG. 4 illustrates an embodiment of a system for determining tension deformation of an object.

FIG. 3 illustrates one of the k SAW devices mounted within a well 83 formed in an object 84 that experiences strain deformation. A top surface 88A of a substrate 88 that carries the IDT 60 and the reflector electrodes 65-69 (shown collectively as a simple block in FIG. 3) faces away from the object 84 and a bottom surface 88B of the substrate 88 is bonded securely to a bottom surface 90A of a well 90 using an adhesive 92, such as solder or another adhesive that stiffens after curing. End and side surfaces of the substrate are also bonded to adjacent surfaces of the well 83 using the adhesive 92. In lieu of the using the adhesive to bond the side and end surfaces to proximate surfaces of the well, a clip is disposed between the side and end surfaces and the well surfaces.

FIG. 3 also illustrates a cover 104 for the SAW sensor. The cover 104 is attached to the object 84 with a soft and yielding adhesive 105. An adhesive with these properties is desired to permit the object 84 to freely deform in response to applied forces, without being constrained by the cover 104.

As illustrated in FIG. 3 it is preferred that the IDT 60 and the reflector array 65-69 are aligned with a top surface 84A of the object 84. This arrangement ensures that the top surface 88A of the substrate 88 is subjected to approximately the same strain deformation as the object 84, resulting in a more accurate strain measurement.

Compression and tension forces applied to the object 84 cause strain deformation of the object. The strain deformation is transferred to the bottom surface 88B of the substrate 88 and through the substrate to the top surface 88A where the SAW waves travel. Thus the top surface 88A of the SAW substrate 88 expands and contracts proportionately with the expansion and contraction of the object's bottom surface 90A due to the application of the compression or tension forces.

A length of arrowheads 100 indicates a magnitude of strain compression of the object 84 as a result of compression forces exerted on the object. A length of arrowheads 102 indicates a magnitude of compression of the substrate 88. As can be seen by comparing the arrowhead lengths, the compression of the substrate 88 is proportional to but less than the compression of the object 84 due to the transfer of the compression forces through the body 84, the bonding material 90, and the substrate 88 to the IDT 60 and the reflector array 65-69.

As described elsewhere herein, when the body 84 is at rest, i.e., no compression or tension forces applied to it, there is strain deformation. Compression forces compress the body 84, the bonding material 90 and the substrate 88 as described above. Tension forces, not shown, expand the body 84, the bonding material 90 and the substrate 88.

Figure 5:
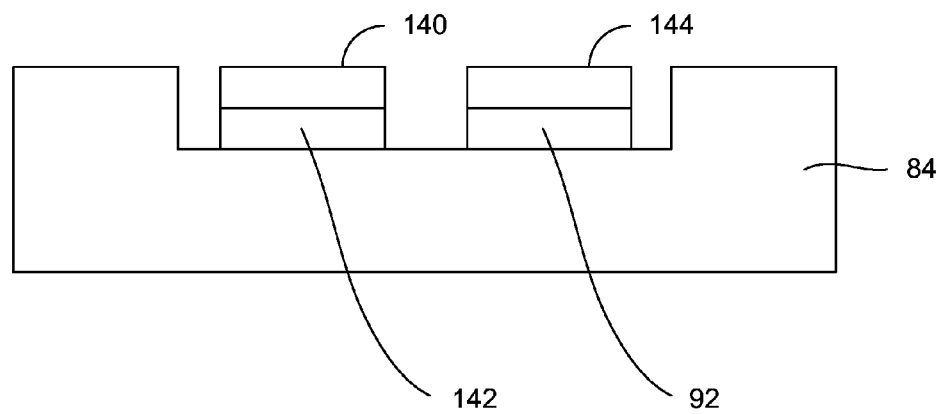
FIG. 5 illustrates an embodiment of a system for determining both strain deformation and temperature of an object.

FIG. 5 illustrates a top view of a SAW-based system for determining tension strain deformation due to the application of tension forces, as depicted by arrowheads 120, on the object 84. A SAW substrate 122 defines a zig-zag pattern in its side surfaces 122A and 122B. Thus the SAW substrate differs from the SAW substrate 88, which defines flat surfaces. The zig-zag pattern side surfaces are more effective when measuring tension deformation than a flat side surface.

While there are many different types of strain deformations as caused by different force vectors, they must each create some physical change in the object 84, the substrate 80 and the SAW components disposed on the top surface of each of the k SAW devices in order to measure the resulting strain. Effectively, the components of the k SAW devices expand or contract proportionally to the expansion or contraction of the object 84 as it responds to applied tension and compression forces.

Because each of the k SAW devices physically expands or contracts in response to forces applied to it, the time domain response of each SAW device also expands or contracts the echo signals. Using digital signal processing techniques, this time domain change can be detected and recorded, if desired.

A database of system time domain responses (or responses in a different domain) to known strains can be created for use in determining the magnitude and type of strain that is being experienced by an object. To create the data base, the object 84 is subjected to various forces that produce strain deformations. The strain deformations are determined by techniques known to those skilled in the art and correlated with each time domain response of the system of k SAW devices. Thus a database of known strain deformations and associated time domain responses can be created. Each one of those responses is stored in a DSP engine as a matched filter. In lieu of subjecting the object 84 to real world forces to create the database, it can be created by simulating the application of forces to an object representing the object 84.

To then determine the strain deformation of the object 84, for example when the object 84 is a component of an operating machine, a time domain response of the operating machine is determined. This response is compared with each one of the matched filter responses during each SAW interrogation cycle and the matched filter yielding the best match is determined. The strain deformation associated with that matched filter represents the strain deformation experienced by the component during operation of the machine.

Because it is not possible to separate temperature effects from strain effects in a SAW reflected signal, it is preferred to mount a temperature-measuring SAW sensor on the same surface (for example, a bottom surface of a well) as the strain-measuring SAW sensor(s). The former SAW sensor is mounted using a soft and yielding but heat conductive adhesive, such as a silicone adhesive. This type of adhesive absorbs strain deformations and thereby minimizes the strain deformations imposed on the temperature-measuring SAW sensor. By separately determining temperature-induced SAW effects and deformation-induced SAW effects a more accurate strain-related deformation can be obtained by removing the temperature-induced SAW effects.

FIG. 5 illustrates a SAW sensor 140 for determining temperature-induced strain effects (attached to a well surface using a soft, yielding and heat-conducting adhesive 142) a SAW sensor 144 for determining strain-induced SAW effects (attached to the well surface using the adhesive 92). The SAW sensors 140 and 144 separately determine deformations of the object 84 so that the temperature-related effects can be removed from the strain determined by the SAW sensor 144.

Although the invention has been shown and described with respect to a certain preferred embodiment or embodiments, equivalent alterations and modifications may occur to others skilled in the art upon the reading and understanding of this specification and the annexed drawings. In particular regard to the various functions performed by the above described components (assemblies, devices, circuits, etc.), the terms used to describe such components are intended to correspond, unless otherwise indicated, to any component that performs the specified function of the described component (i.e., that is functionally equivalent), even though not structurally equivalent to the disclosed structure, which performs the function in the illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A senor system for determining deformation of an object subject to forces, the sensor system comprising:
    an object upon which forces are exerted and defining a cavity therein;
    a first substrate for supporting surface acoustic waves in an upper surface of the first substrate, the first substrate disposed in the cavity;
    a first surface acoustic wave transducer disposed on the upper surface and responsive to an interrogation signal for generating an incident surface acoustic wave in the upper surface;
    a first reflector array responsive to the incident surface acoustic wave for creating reflected surface acoustic waves on the upper surface, characteristics of the reflected surface acoustic waves responsive to strain deformation of the object due to a force exerted on the object;
    the first surface acoustic wave transducer responsive to the reflected surface acoustic waves and for generating an electrical signal responsive thereto;
    a radio frequency (RF) transceiver for receiving the electrical signal and for determining deformation of the object responsive thereto;
    a second substrate affixed to the object or disposed within the cavity and spaced apart from the first substrate, a second surface acoustic wave transducer and a second reflector array both mounted on the second substrate for determining a temperature proximate the first substrate; and
    wherein the first substrate is affixed in the cavity with a stiff adhesive and the second substrate is affixed to the object or disposed within the cavity with a soft and yielding bonding material.

2. The sensor system of claim 1 wherein the first reflector array comprises a plurality of acoustic wave reflectors, a reflected signal from each one of the plurality of reflectors having a phase shift caused by a spacing between each reflector of the reflector array.

3. The sensor system of claim 1 the first transducer responsive to a plurality of serial interrogation signals, each generating an incident surface acoustic wave, the first reflector array creating a like plurality of reflected surface acoustic waves, a reference correlation peak of the reflected surface acoustic waves created when no forces are exerted on the object, a first correlation peak of the reflected surface acoustic waves created when a force is exerted on the object and having a time offset from the reference correlation peak, the time offset indicative of an amount of deformation of the object.

4. The sensor system of claim 3 wherein a time offset $\Delta t$ prior to a time $t_0$ of the reference correlation peak indicates a compressive strain deformation of the object and a time offset $\Delta t$ after the reference correlation peak time indicates an expansive strain deformation of the object.

5. The sensor system of claim 4 wherein a magnitude of $\Delta t$ is responsive to a magnitude of deformation of the object, which is responsive to a magnitude of a tension or compression force exerted on the object.

6. The sensor system of claim 1 wherein the first surface acoustic wave transducer comprises an interdigital transducer.

7. The sensor system of claim 1 wherein a characteristic of the reflected surface acoustic waves comprises a delayed correlation peak.

8. The sensor system of claim 1 further comprising k surface acoustic wave sensors each comprising a transducer and a reflector array, where $p_k$ is defined as a distance between a transducer and a first reflector in each of the k sensors, wherein $p_k$ is different for each of the k sensors.

9. The sensor system of claim 1 wherein the temperature is determined from a response characteristic of reflected surface acoustic waves from the second reflector array.

10. The sensor system of claim 1, wherein deformation effects due to the temperature are separated from deformation effects due to the force exerted on the object.

11. The sensor system of claim 1 wherein the first surface acoustic wave transducer and the first reflector array are substantially aligned with an upper surface of the object.

12. A sensor system for determining deformation of an object subject to forces, the sensor system comprising:
an object upon which forces are exerted and defining a cavity therein;
a substrate for supporting surface acoustic waves in an upper surface of the substrate, the substrate disposed in the cavity;
a surface acoustic wave transducer disposed on the upper surface and responsive to an interrogation signal for generating an incident surface acoustic wave in the upper surface;
a reflector array responsive to the incident surface acoustic wave for creating reflected surface acoustic waves on the upper surface, characteristics of the reflected surface acoustic waves responsive to strain deformation of the object due to a force exerted on the object;
the surface acoustic wave transducer responsive to the reflected surface acoustic waves and for generating an electrical signal responsive thereto;
a radio frequency (RF) transceiver for receiving the electrical signal and for determining deformation of the object responsive thereto;
wherein a lower surface of the substrate is affixed to a bottom surface of the cavity with a stiff bonding material; and
wherein the substrate further comprises two end surfaces and two side surfaces, wherein one or both of the two end surfaces and the two side surfaces are affixed to proximate surface of the cavity with a stiff bonding material.

13. A sensor system for determining deformation of an object subject to forces, the sensor system comprising:
an object upon which forces are exerted and defining a cavity therein;
a first substrate for supporting surface acoustic waves in an upper surface of the first substrate, the first substrate disposed in the cavity;
a first surface acoustic wave transducer disposed on the upper surface and responsive to an interrogation signal for generating an incident surface acoustic wave in the upper surface;
a first reflector array responsive to the incident surface acoustic wave for creating reflected surface acoustic waves on the upper surface, characteristics of the reflected surface acoustic waves responsive to strain deformation of the object due to a force exerted on the object;
the first surface acoustic wave transducer responsive to the reflected surface acoustic waves and for generating an electrical signal responsive thereto;
a radio frequency (RF) transceiver for receiving the electrical signal and for determining deformation of the object responsive thereto; and
wherein opposing side surfaces of the first substrate define a zig-zag profile.

14. A sensor system for determining deformation due to one or more forces applied to an object, the sensor system comprising:
an object upon which forces are exerted and defining a cavity therein;
a plurality of SAW sensors disposed in the cavity for determining deformation of the object in a plurality of directions, at least one of the plurality of SAW sensors comprising a first substrate defining relatively smooth side surfaces and at least one of the plurality of SAW sensors comprising a second substrate defining a zig-zag pattern in the side surfaces;
a temperature-determining SAW sensor; and
wherein deformation effects due to the temperature of the object are separated from deformation effects due to one or more forces applied to the object.

15. The sensor system of claim 14 wherein the SAW sensors for determining deformation are affixed to one or more cavity surfaces using a stiff bonding material and the temperature-determining SAW sensor is affixed to one or more cavity surfaces using a soft and yielding bonding material.

16. The sensor system of claim 14 wherein an upper surface of each SAW sensor for determining deformation is substantially aligned with an upper surface of the object.

* * * * *